United States Patent [19]
Czeisler et al.

[11] Patent Number: 5,146,927
[45] Date of Patent: Sep. 15, 1992

[54] TEST FOR EVALUATION OF VISUAL FUNCTIONING IN VISUALLY IMPAIRED SUBJECTS

[75] Inventors: Charles A. Czeisler, Cambridge; Heinz Martens, Jamacia Plain, both of Mass.; Theresa L. Shanahan, Madison, Wis.

[73] Assignee: Brigham and Women's Hospital, Boston, Mass.

[21] Appl. No.: 714,154

[22] Filed: Jun. 14, 1991

[51] Int. Cl.$^5$ .............................................. A61B 13/00
[52] U.S. Cl. ..................................... 128/745; 600/27; 351/222; 351/246
[58] Field of Search .................. 128/745, 395; 600/26, 600/27; 514/416, 415, 419, 455; 351/200, 246, 221, 222

[56] References Cited

U.S. PATENT DOCUMENTS

| | | | |
|---|---|---|---|
| 4,600,723 | 7/1986 | Short et al. | 514/416 |
| 4,858,609 | 8/1989 | Cole | 128/395 |

OTHER PUBLICATIONS

Arendt et al., *The Lancet*, 772–773 (1988) "Synchronisation of a Disturbed Sleep–Wake Cycle . . .".
Czeisler et al., *Science* 233:667–671 (1986) "Bright Light Resets the Human Circadian . . .".
Czeisler et al., *Science* 217:460–463 (1982) "Rotating Shift Work Schedules . . .".
Czeisler et al., *Science* 210:1264–1267 (1980) "Human Sleep: Its Duration . . .".
Czeisler et al., *N. Engl. J. Med.* 322:1253–1259 (1990) "Exposure to Bright Light and Darkness . . . ".
Folkard et al., *Neuroscience Letters* 113:193–198 (1990) "Melatonin Stabilises Sleep . . .".
Fraser et al., *Clin. Chem.* 29:396–397 (1983) "Direct Radioimmunoassay for Melatonin in Plasma".
Klein et al., *Brain Research 174:245–262 (1979)* "Pineal N–Acetyltransferase . . .".
Lewy et al., *Science* 210:1267–1269 (1980) "Light Suppresses Melatonin Secretion in Humans".
Lewy et al., *J. Clin. Endocrinol. Metab.* 56:1103–1107 (1983) "Different Types of Melatonin . . .".
Martens et al., *Sleep Res.* 19:398 (1990) "Sleep/Wake Distribution . . .".
Martens et al., Abstract Form for Sleep Res., Cat. #20 WFSRS Founding Congress, Cannes, France Sep. 21-25, 1991 "Chronic Non-24-Hour Sleep/Wake Disorder . . .".
McIntyre et al., *J. Pineal Res.* 6:149–156 (1989) "Human Melatonin Suppression . . .".
Miles et al., *Sleep Res.* 6:192 (1977) "High Incidence of Cyclic Strap Sleep/Wake Disorders in the Blind."
Miles et al., *Science* 198:421–423 (1977) "Blind Man Living in Normal Society . . .".
Orth et al., *Clin. Endocrinol.* 10:603–617 (1979) "Free–Running Circadian . . .".
Rusak, *J. Comp. Physiol.* 118:165–172 (1977) "Involvement of the Primary Optic Tracts . . .".
Sack et al., *J. Pineal Res.* 3:379–388 (1986) "Human Melatonin Production Decreases with Age".
Sack et al., *Sleep Res.* 18:441 (1989) "Cortisol and Melatonin . . .".
Sewitch et al., *Biol. Psychiatry* 21:201–207 (1986) "Alpha-NREM Sleep . . .".
Shanahan et al., *Melatonin and Temperature Rhythms Are Coupled*, Second Annual Meeting of the Society for Research on Biology Rhythms, Jacksonville, FL May 9–13, 1990 "Light Exposure Induces . . .".
Smith et al., *The Lancet*, 933 (1981) "Altered Diurnal Serum Melatonin Rhythm in Blind Men".
Waldhauser et al., *Melatonin in Humans*, 179–191 Vienna, Austria (1985) "Changes in Melatonin . . .".

*Primary Examiner*—Max Hindenburg
*Assistant Examiner*—Guy V. Tucker
*Attorney, Agent, or Firm*—Sterne, Kessler, Goldstein & Fox

[57] ABSTRACT

A method of determining the functional integrity of the visual system (including the photoreceptive elements, the retino-hypothalamic tracts and their connections to the suprachiasmatic nuclei of the hypothalamus) of visually imparied human beings. The method includes measuring the melatonin content in blood samples taken before, during and after application of a stimulus (e.g. light) to the subject's retinas, and comparing the measured melatonin content to determine if the melatonin content was suppressed during application of the stimulus.

20 Claims, 6 Drawing Sheets

TEST FOR EVALUATION OF VISUAL FUNCTIONING IN VISUALLY IMPAIRED SUBJECTS

STATEMENT AS TO RIGHTS TO INVENTIONS MADE UNDER FEDERALLY-SPONSORED RESEARCH AND DEVELOPMENT.

Part of the work performed during development of this invention utilized U.S. Government funds. The U.S. Government has certain rights in this invention.

FIELD OF THE INVENTION

This invention relates to a test for evaluating visual functioning, and more specifically to a test for determining the functional integrity of the retino-hypothalamic tracts of visually impaired humans by measuring their melatonin secretion in response to a stimulus.

BACKGROUND OF THE INVENTION

Human beings alternate regularly between the states of sleep and wakefulness in a cycle that is normally in synchrony with the periodic rotation of the earth and with many geophysical phenomena such as the daily light-dark cycle. Sleep and wakefulness are normally consolidated into separate episodes with sleep occurring during the darkness at night and wakefulness occurring during the light of the day. Sleep, body temperature and plasma hormone concentrations and other constituents vary rhythmically in young adults living on a regular day-night schedule FIG. 1). Under normal conditions, these physiological rhythms, which have a variety of waveforms, have their own characteristic phase relationship with each other and with the twenty-four hour light-dark cycle.

In the absence of the periodic time cues of the external environment (e.g., sunrise and sunset), the cycle length or free-running period of daily oscillations of these rhythms is no longer synchronized or entrained to a twenty-four hour period. In humans, the free-running period is nearly always close to but not exactly equal to twenty-four hours. Hence the term circadian (circa=-about, and dies=day) is used to describe these rhythms. In healthy young adult subjects, the average free-running period of the synchronized circadian system is longer than twenty-four hours. In other words, in the absence of periodic external cues, the internal biological clock runs a little slower than its mechanical or geophysical counterparts.

Under free-running conditions it is not only the sleep-wake cycle which remains periodic, but also many underlying physiological functions such as the core body temperature cycle and the secretion of melatonin from the pineal gland. Melatonin (N-acetyl-5-methoxytryptamine) is a hormone that is normally secreted by the human pineal gland almost exclusively at night. One hypothesized function of the hormone melatonin is the transmission of information about the presence of light and dark to body tissues for temporal regulation of other body functions.

The suprachiasmatic nuclei, located in the hypothalamus of the human brain just above the optic chiasm, are believed to be the central neural pacemaker which coordinate inter-dependent circadian rhythms and synchronize their cycle length to periodic external cues FIGS. 2 and 3). In 1972 it was demonstrated that a pair of subcortical monosynaptic pathways, the retino-hypothalamic tracts, link each human retina with the SCN. Studies have since shown that the retino-hypothalamic tracts are critical pathways for the transmission of visual information required for proper functioning of the human circadian system in accordance with a twenty-four hour day.

In particular, it has been found in mammals that bilateral transection of the optic nerve interrupts both the retino-hypothalamic tract and the optic tract, leading to blindness and a complete loss of synchronization or entrainment of the circadian system to the twenty-four hour day. In contrast, entrainment is maintained after bilateral transection of the primary optic tract which leaves the retino-hypothalamic tract intact, but the animal behaviorally blind. Therefore, the retino-hypothalamic tract is a critical pathway for transmission of the visual information required for entrainment of the circadian cycle to a twenty-four hour day. In addition, the retino-hypothalamic tract is a critical pathway for transmission of visual information from the retina to the SCN and from the SCN to the pineal gland (see FIG. 2).

Information that is transmitted along this pathway includes the presence or absence of environmental light. It has been found that light, and the absence thereof, has an effect on the secretion of melatonin from the pineal gland in humans. It was demonstrated in studies by Lewy et al. that bright light applied to the human retina during the subjective night, when melatonin secretion (the timing of which is regulated by the SCN) is normally high, will suppress such secretion. "Light Suppresses Melatonin Secretion in Humans," Lewy et al., *Science*, Vol. 210. Dec. 12, 1980, pp. 1267–69. The ability to artificially suppress human melatonin secretion is an important indicator that light signals reach the circadian clock located in the SCN (i.e., that the subject possesses residual photic input). The ability to synchronize the human circadian pacemaker to the twenty-four hour light-dark cycle is contingent upon the proper functioning of the retino-hypothalamic tract of the human, which as noted above is the passageway for transmitting the presence of stimuli from the retina to the SCN.

Many chronic sleep disturbances are associated with abnormalities in the human circadian rhythms such as the core body temperature cycle and melatonin secretion. When these rhythms are entrained, the human is synchronized to a twenty-four hour daily cycle. On the other hand, when these rhythms are not synchronized, the human is likely to experience chronic sleep disturbances (e.g. insomnia). Czeisler et al. have previously described a method for synchronizing the human circadian pacemaker. Czeisler et al., "Light Resets the Human Circadian Pacemaker Independent of the Timing of the Sleep-Wake Cycle," *Science* 233:667-71 (Aug. 8, 1986). The method involves the application of light and dark stimuli to a subject at a predetermined time in order to shift a subject's normal rest-activity cycle to a desired cycle. The advantages to such a shift are numerous and include the ability to overcome jet lag, adjust to shift work, and to simply wake at a routine time without being groggy.

It has been discovered that a dysfunctioning retino-hypothalamic tract is unable to transmit the presence of stimuli to the brain in order to achieve synchronization or phase shifts of the circadian pacemaker in response to light. However, as noted above, a dysfunctioning primary optic tract (resulting in the inability to perceive light and dark) are not always indicative of a dysfunctioning retino-hypothalamic tract. Furthermore, damage to the occipital cortex (the region of the brain responsible for the conscious processing of visual information) or to the retina can also result in the inability of the subject to perceive light and dark, yet these dysfunctions are not always indicative of a dysfunctioning retino-hypothalamic tract. That is, a subject can be behaviorally blind (unable to perceive light and dark) and still have a functioning retino-hypothalamic tract. Preliminary tests by applicants have shown that a majority of blind humans suffer from disrupted sleep characterized by numerous nocturnal arousals and excessive daytime sleepiness. However, because of the perception that blind individuals are not responsive to light, it was believed that exposure to artificial or natural light stimuli had no effect on entrainment of the endogenous circadian pacemaker. Thus, preservation of residual visual input was not believed to be of importance to such subjectively "blind" patients and as a result, therapy such as dark glasses which reduce the input of light to the visual system are often used. Such behavior may worsen the occurrence of severe chronic sleep disturbances in blind humans. Similarly, aging is associated with a functional decrease in vision, possibly leading to a decreased input of photic information to the SCN. Diminishing ocular input to the SCN may be partly responsible for age-related changes in the circadian timing system.

Preliminary data suggests that preserving visual input in blind patients may be of great importance as even a residual input may be capable of keeping the circadian pacemaker in synchrony with the 24-hour day and thus preventing the onset of a severe and chronic sleep disorder. If the circadian pacemaker in some blind individuals is responsive to bright light pulses administered during the melatonin suppression test of the present invention, therapeutic trials to synchronize their biological clocks by critically timed bright light exposure could be considered. Further evaluation of blind patients who suffer from sleep disturbances will be possible along with suggestions regarding their living habits (e.g., to avoid wearing dark glasses or to spend time outdoors at certain times of day; to expose themselves to artifical bright light sources at critical times).

Thus, the need exists for a method of evaluating the functional integrity of the human visual system (including the photoreceptive elements, the retino-hypothalamic tract and its connections to the SCN) which mediates photic input from the retina to the hypothalamus, and in particular, the visual system of a behaviorally blind or visual impaired human being. Such an evaluation is especially helpful in determining if the visual system is sufficiently intact for entrainment of the circadian pacemaker.

SUMMARY OF THE INVENTION

The present invention may be described as a method of determining the functional integrity of the visual system which mediates photic input from the retina to the hypothalamus of a visually impaired human subject by measuring the melatonin secretion of the subject comprising the steps of collecting a first blood sample from the subject, thereafter exposing the subject to a bright light stimulus, collecting a second blood sample from said subject during exposure to the stimulus, measuring the melatonin content in the first and second collected samples, and comparing the measured melatonin content in the first and second collected samples to determine whether the melatonin content in the second collected sample is less than the melatonin content in the first collected sample to thereby evaluate the functional integrity of the retino-hypothalamic tract of the subject.

The method may further comprise the steps of predicting the minimum of the endogenous circadian temperature cycle of the subject and exposing the subject to the stimulus at a time determined by the predicted minimum of the endogenous circadian temperature cycle of the subject. The time at which exposure occurs may be centered approximately 1.5 hours before the predicted minimum of the endogenous circadian temperature cycle of the subject. The stimulus may be applied to the subject for a time period which is greater than approximately one hour.

The method may further comprise the steps of collecting a third blood sample from the subject after exposure to the stimulus, measuring the melatonin content in the third collected sample, and comparing the measured melatonin content of the third collected sample to the measured melatonin content of the second collected sample to determine whether the measured melatonin content in the second collected sample is less than the measured melatonin content in the third collected sample to thereby evaluate the functional integrity of the retino-hypothalamic tract of the subject.

The minimum of the endogenous circadian temperature cycle of the subject may be predicted by measuring the core body temperature of the subject over a twenty-four hour period and plotting the measured temperature on a graph. The first collected blood samples may be a plurality of first blood samples collected over a period of time. Similarly, the second collected blood samples may be a plurality of blood samples collected over a period of time. The first and second plurality of blood samples may be collected at approximately thirty minute intervals. The melatonin content of the collected samples may be determined using an assay. The bright light stimulus may be greater than approximately 2000 lux and may be applied to the subject for greater than approximately one hour, and for approximately two to four hours. The measured melatonin content of the first and second samples may be compared by plotting on a graph. The stimulus may be applied to a retina of said subject.

In addition, the present invention may be characterized as a method of determining the functional integrity of the visual system which mediates photic input from the retina to the hypothalamus of a visually impaired human subject by measuring the melatonin secretion of the subject comprising the steps of predicting the minimum of the endogenous circadian temperature cycle of the subject, collecting a first blood sample from the subject, thereafter exposing the subject to a bright light stimulus of greater than approximately 2000 lux at approximately 1.5 hours before the predicted minimum of the endogenous circadian temperature cycle of the subject, collecting a second blood sample from the subject during exposure to the stimulus, collecting a third blood sample from the subject after exposure to the stimulus, measuring the melatonin content in the first, second and third collected samples, and comparing the measured melatonin content in the first, second and third collected samples to determine whether the measured melatonin content in the second collected sample is less than said measured melatonin content in the first and/or third collected sample to evaluate the functional integrity of the retino-hypothalamic tract of the subject. The bright light stimulus may be approximately 2,500 to 10,000 lux, and a plurality of first, second and third blood samples may be collected at approximately thirty minute intervals.

These and other features and advantages of the present invention will become more apparent as the invention is further described below.

DETAILED DESCRIPTION OF THE PREFERRED EMBODIMENTS

The method of the present invention is designed to evaluate the functional integrity of the human subcortical or subconscious visual system in visually impaired subjects. The terms subcortical or subconscious visual system as used throughout this application refer to the photoreceptive elements, the retino-hypothalamic tract and its connection to the suprachiasmatic nuclei (SCN) which collectively mediate photic input from the retina to the human circadian pacemaker located in the hypothalamus. The method finds particular use with the visually impaired as a means for identifying visual input and treating the preservation thereof; as well as for determining suitability of a visually impaired individual for entrainment of their endogenous circadian cycles (e.g., rest-activity schedule). The term visually impaired as used throughout this application refers not only to persons that are diagnosed as "blind" (inability to perceive light and dark), but also to individuals that have diminished ocular input of photic information to the SCN.

In summary, the method of the present invention involves the administration of one to two hours of bright light (approximately 2,500 to 10,000 lux) at the time of the expected maximum of the melatonin secretion rhythm of the subject and collecting frequent blood samples from the subject for plasma melatonin analysis before (for approximately four to eight hours), during and after (for approximately four to eight hours) the application of the light stimulus. The melatonin content in the samples is compared to determine if the melatonin content in the samples taken during the application of the stimulus is less than the content in the samples taken before and/or after application of the stimulus. A determination that the content was less during application of the stimulus indicates that the stimulus suppressed melatonin secretion. Suppression of melatonin secretion caused by application of a bright light stimulus is an indication that the subconscious visual system of the subject is at least partially intact and that steps should be taken to preserve residual visual input. The method of the present invention will now be described in greater detail below.

Figure 5:
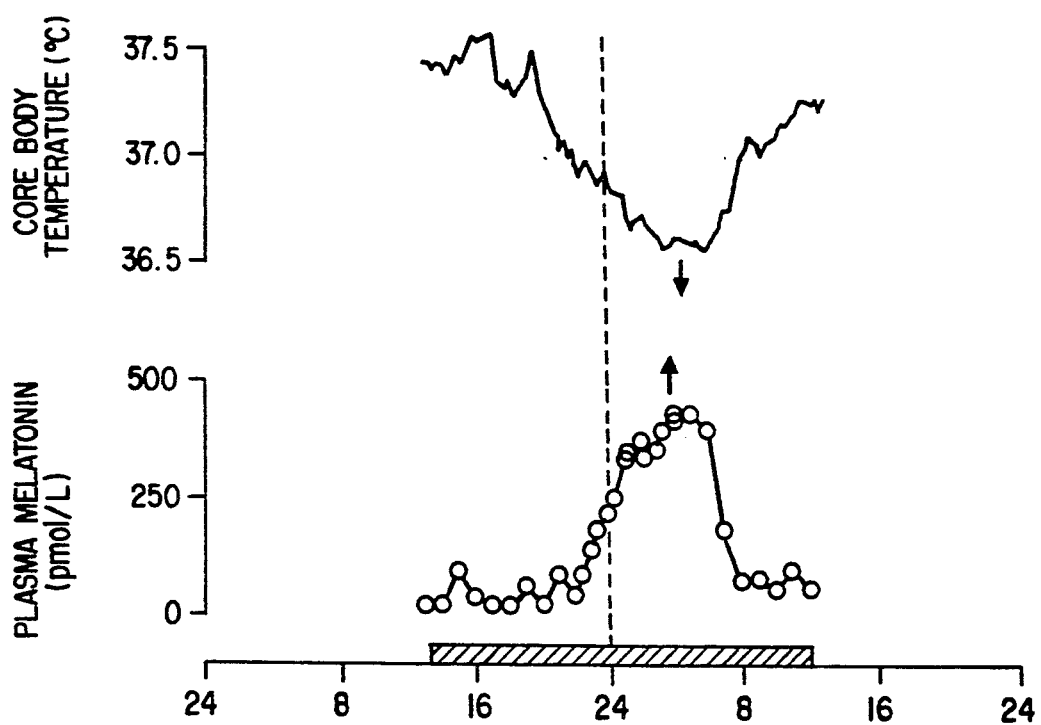
FIG. 5 is a chart showing the relationship between core body temperature and plasma melatonin observed under a constant routine condition in a young adult living on a regular day-night schedule.

As FIG. 5 shows, the core body temperature of a young adult living on a constant routine has a rhythm that reaches a nadir between 03:00 and 06:00, but decreases significantly between 24:00 and 06:00 (the latter half of the habitual sleep/dark episode). Conversely, the natural rhythm of the secretion of melatonin consists of a significant increase during the habitual sleep/dark episode of the day. Studies have shown that maximum melatonin secretion in young adults living on a regular day-night schedule typically occurs approximately 1.5 to 2 hours before the minimum of the core body temperature rhythm. Thus, for optimum results, the test of the present invention should be centered around the period of maximum melatonin secretion. Accordingly, application of the stimulus should be centered twenty-two and one-half hours after the estimated initial core body temperature minimum of the subject and continue for approximately one to four hours. Application of the stimulus is described in greater detail below.

Figure 6:
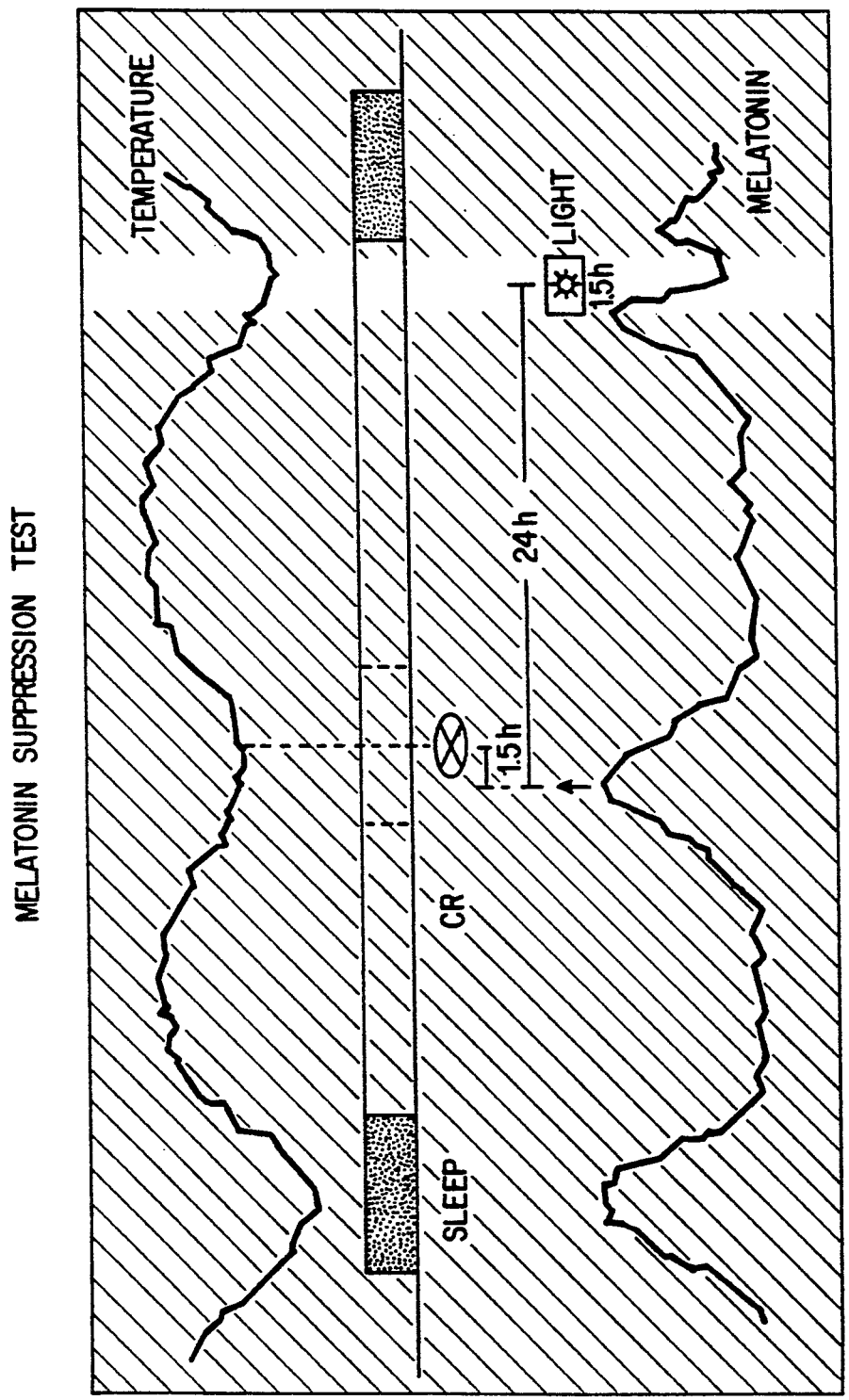
FIG. 6 is a diagram illustrating the method of the present invention.

The test lasts approximately forty to sixty-four hours. During administration of the test, the subject should be confined to an individual room or suite where external time cues (such as clocks, radios and sunlight) are non-existent or limited. Optimally, the room temperature should be maintained at 71° to 77° F. with the light in the room maintained constant (at 150 lux or less) other than when the stimulus is applied. Referring now to FIG. 6 in which a chart illustrating the method of the present invention is shown, the test is begun in the morning following normal night sleep of the subject. Upon waking, the subject is maintained in the room in a semi-recumbent position. The subject's core body temperature is measured continuously (by a rectal temperature thermistor) as noted in the top panel of the Figure. Blood samples are taken at twenty to thirty minute intervals throughout the test through an indwelling intravenous catheter placed in a forearm vein. The charted melatonin content of the blood samples is shown in the bottom panel of FIG. 6. The middle panel of the Figure indicates the sleep/wake periods of the subject. On night one (the black box on the left), the subject goes to sleep at their habitual bedtime and wakes at their habitual wake time.

Figure 1:
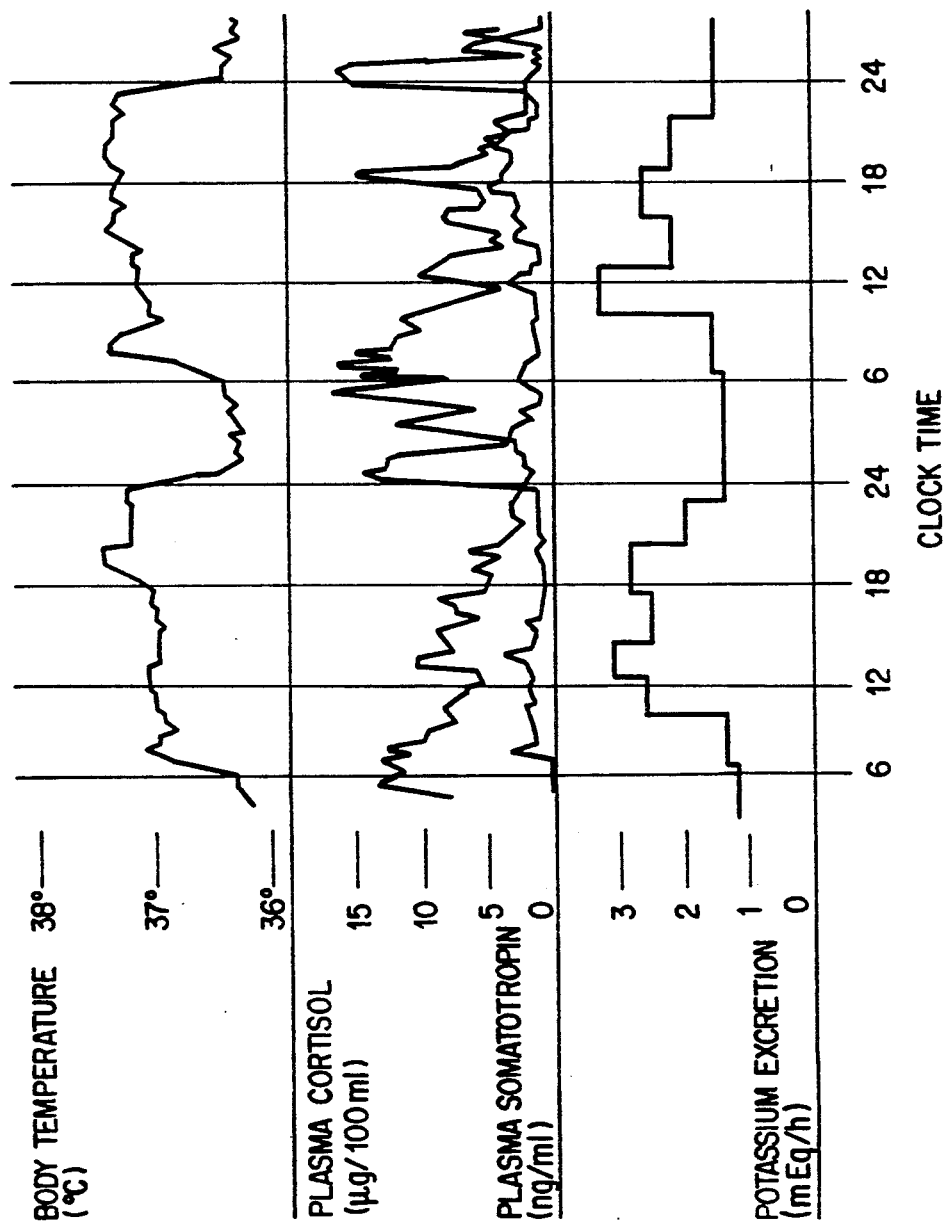
FIG. 1 is a chart showing the relationship between core body temperature, plasma cortisol, somatotropin concentrations and renal potassium excretion in a young adult living on a regular day-night schedule.
Figure 2:
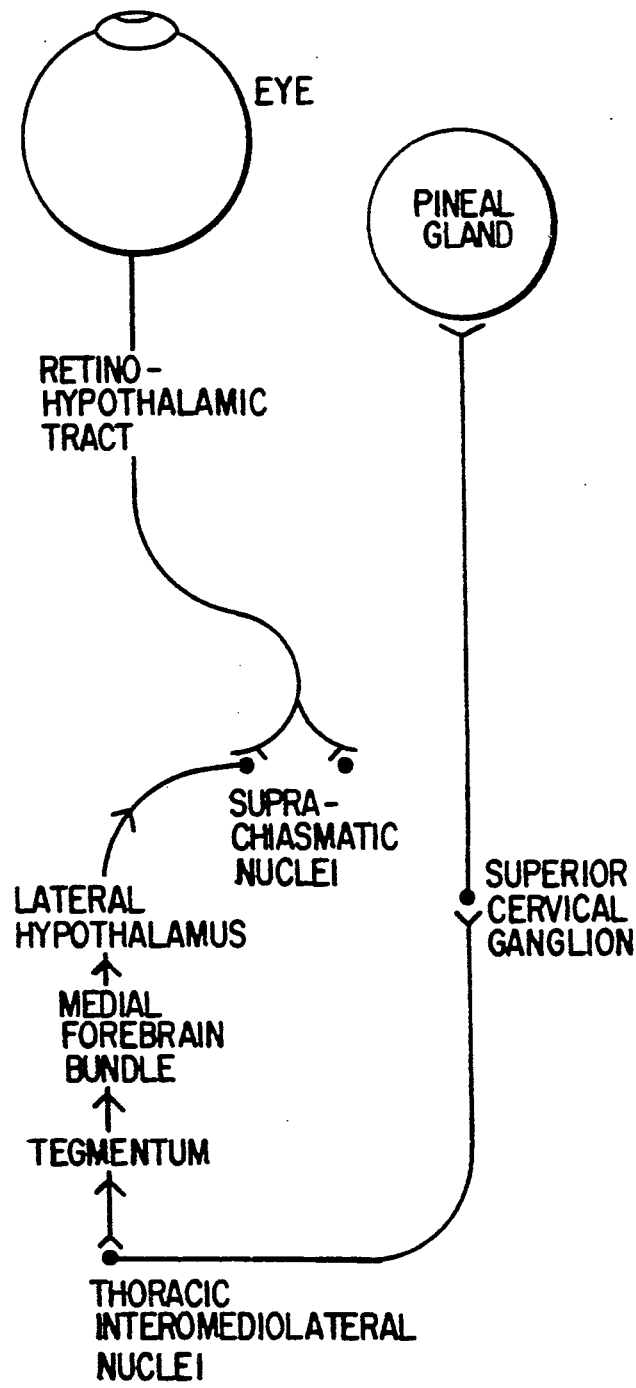
FIG. 2 is a schematic drawing of the neuroanatomical connections from the retina to the pineal gland.
Figure 3:
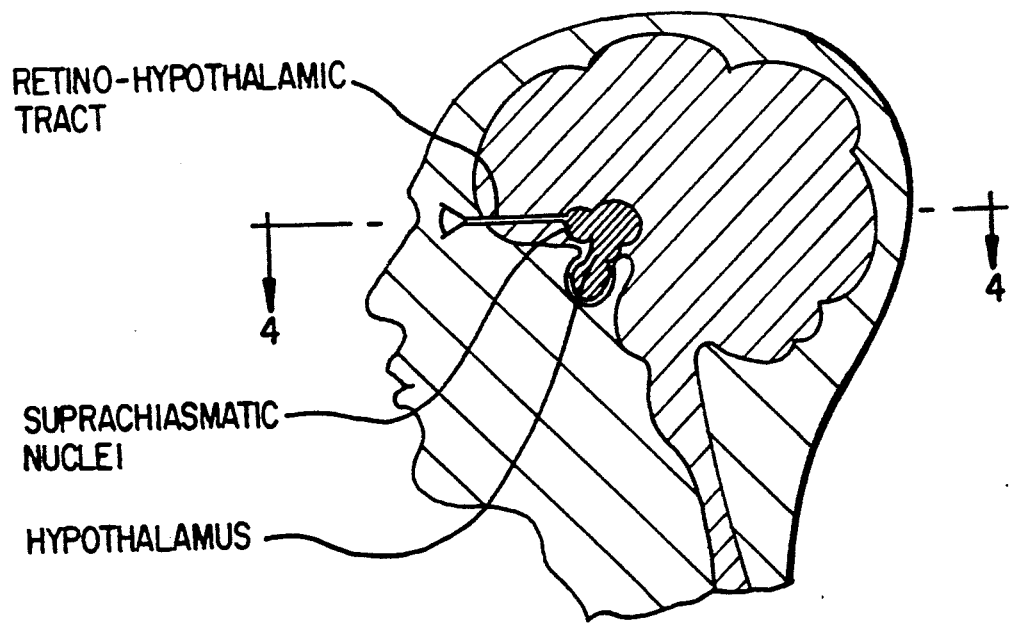
FIG. 3 is a schematic drawing of the human visual system and brain.
Figure 4:
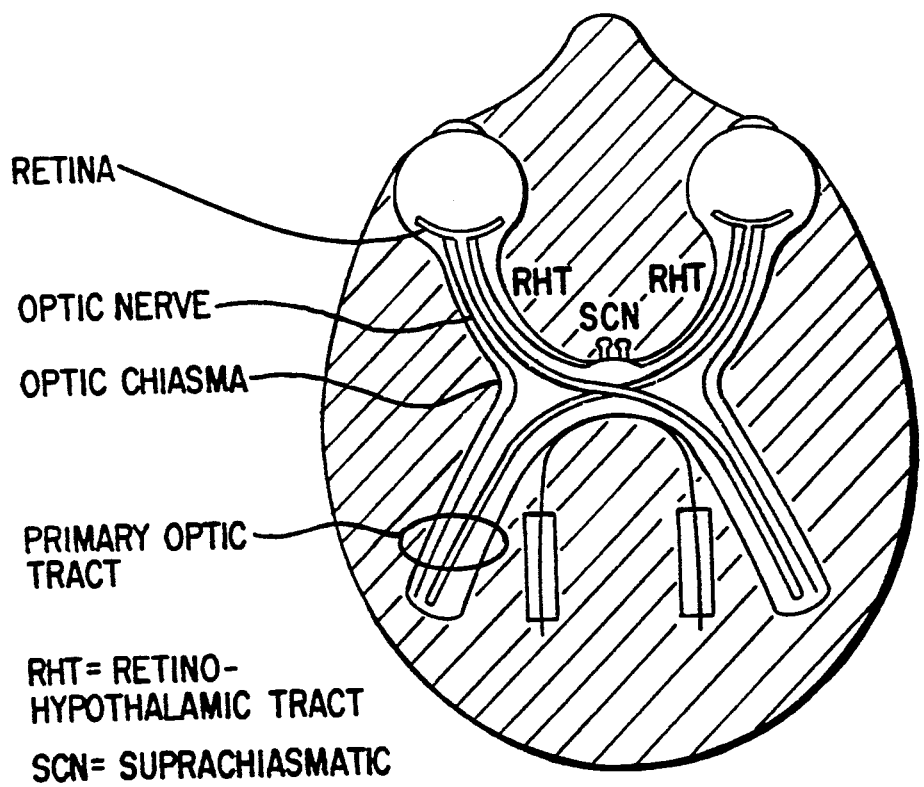
FIG. 4 is a cross-section taken along line 4—4 in FIG. 3.

For the forty hours between night one and night three (the black box on the right) the subject is kept awake on a constant routine (CR). For a discussion of a suitable CR, see Czeisler et al., "Exposure to Bright Light and Darkness to Treat Physiological Maladaptations to Night Work," *The New England Journal of Medicine* 322:1253–59 (May 3, 1990). During the CR, the subject is given a regimen of enforced semirecumbent wakefulness in constant indoor light (indicated by the stippled area of FIG. 4), with nutritional intake divided into hourly snacks and with activity restricted to prevent changes in body posture and activity level that could affect core body temperature. The vertical dotted lines along the sleep/wake period of the middle panel of FIG. 4 indicate the period during which the subject would normally be sleeping, but is kept awake during the CR. The vertical dotted line extending from the temperature curve of the top panel to the (X) in the middle panel indicates the minimum of the subject's core body temperature, preceded by 1.5 hours by the maximum of the melatonin secretion level of the subject (the arrow in the bottom panel). Application of the light stimulus (the white vertical bar) is centered around the time twenty-two and one-half hours (22.5 h) after the minimum of the body temperature cycle and continues for one and one half hours (1.5 h). Following stimulus exposure, the subject is again allowed to sleep. The test is completed the following morning when the subject wakes. It may not be necessary that the subject be awake throughout the test, although exposure of the stimulus to the retina(s) is essential.

The stimulus should be applied to the retina(s) of the subject for approximately a one to four hour interval centered around the predicted minimum of the circadian temperature cycle of the subject. The stimulus is preferably a bright light of greater than 2,000 and preferably about 2,500 to 10,000 lux applied for approximately 1.5 hours. This light intensity is greater than normally required to suppress melatonin secretion in sighted subjects.

Figure 7:
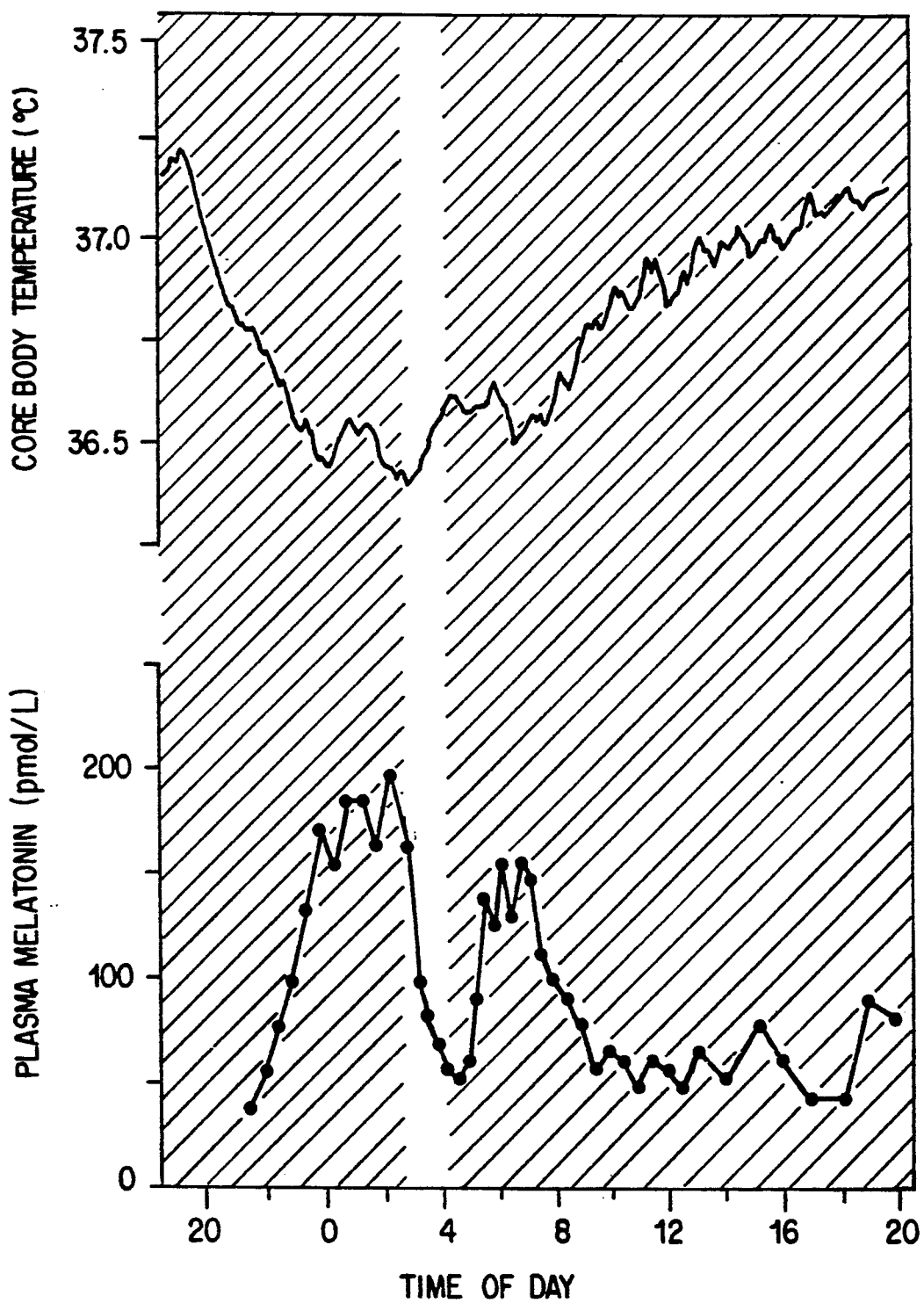
FIG. 7 is a chart showing one example of the application of the method of the present invention and the results achieved by such application in a blind human subject with no conscious light perception.

The plasma melatonin concentrations may be measured following radioimmunoassay according to any known techniques. The sample should be centrifuged at 4° C. to separate the plasma which may then be frozen at −20° C. until it is assayed. The measured melatonin content of the blood samples taken before, during and after application of the stimulus may then be compared to determine if the content was less during application of the stimulus than the content before and/or after application of the stimulus. The measurements can be plotted on a chart with an x axis representing the time of day and the y axis representing the melatonin content (See FIG. 7).

Where the result of this test indicates a suppression of the melatonin secretion of the subject during application of the stimulus (the white vertical bar in FIG. 7), part of the visual system of the subject is functioning, and may be sufficiently intact for entrainment of the circadian pacemaker, presumably through the retino-hypothalamic tract. This is possible despite a lack of visual information reaching consciousness. Applicants have demonstrated that even minimal electrophysiological retinal photoreceptor activity is able to mediate suppression of nocturnal melatonin secretion. The present invention has proven to be more sensitive than a neuro-ophthalmological examination, even with the assistance of electrophysiological tests, in detecting visual input to subcortical regions of the brain. The present invention has implications for the care of visually impaired persons, particularly in determining the necessity of preservation of residual visual input.

An alternative procedure to the one described above is somewhat simpler from a practical point of view and thus is more feasible with regard to a possible clinical use of the test. The method described above predicts the maximum of the melatonin secretion cycle using an estimate of the minimum of the endogenous core body temperature cycle of the subject measured over a prior twenty-four hour period. In the alternative procedure, the subject is kept awake over a single twenty-four hour period during which the subject is exposed to several bright light pulses timed throughout the twenty-four hours. The expectation is that one of the pulses will "hit" the peak (or near to the peak) of melatonin secretion to induce suppression of plasma melatonin levels. As in the previously described embodiment blood sampling should occur at twenty to thirty minute intervals. The advantage of this alternation procedure is that the time period for the test is reduced to twenty-four hours. The disadvantage is that the stimulus may miss being applied at the melatonin cycle peak and therefore, a true indication of melatonin suppression may also be missed.

While the invention has been particularly shown and described with reference to the preferred embodiments thereof, it will be understood by those skilled in the art that the foregoing and other changes in form and detail may be made without departing from the spirit and scope of the invention as set forth in the appended claims.

What we claim is:

1. A method of determining the functional integrity of the visual system mediating photic input from the retina to the hypothalamus of a visually impaired human subject by measuring the melatonin secretion of said subject, comprising the steps of:
   collecting a first blood sample from said visually impaired human subject;
   thereafter exposing said subject to a bright light stimulus;
   collecting a second blood sample from said subject during said exposure to said stimulus;
   measuring the melatonin content in said first and second collected samples; and
   comparing the measured melatonin content in said first and second collected samples to determine whether said melatonin content in said second collected sample is less than the melatonin content in said first collected sample to thereby evaluate the functional integrity of the visual system of said subject.

2. The method of claim 1, further comprising the steps of:
   predicting the minimum of the endogenous circadian temperature cycle of said subject; and
   exposing said subject to said stimulus at a time determined by said predicted minimum of the endogenous circadian temperature cycle of said subject.

3. The method of claim 2, wherein said time is centered approximately 1.5 hours before said predicted minimum of the endogenous circadian temperature cycle of said subject.

4. The method of claim 3, wherein said stimulus is applied to said subject for greater than approximately one hour.

5. The method of claim 2, further comprising the steps of:
   collecting a third blood sample from said subject after said exposure to said stimulus;
   measuring the melatonin content in said third collected sample; and
   comparing the measured melatonin content of said third collected sample to the measured melatonin content of said second collected sample to determine whether said measured melatonin content in said second collected sample is less than the measured melatonin content in said third collected sample to thereby evaluate the functional integrity of the visual system of said subject.

6. The method of claim 2, wherein the minimum of the endogenous circadian temperature cycle of said subject is predicted by:
   measuring the core body temperature of said subject over a forty to sixty-four hour period; and
   plotting said measured temperature on a graph.

7. The method of claim 1, wherein a plurality of first blood samples are collected.

8. The method of claim 7, wherein a plurality of second blood samples are collected.

9. The method of claim 8, wherein said first and second plurality of blood samples are collected at approximately thirty minute intervals.

10. The method of claim 1, wherein the melatonin content of said collected samples is determined using an assay.

11. The method of claim 1, wherein said bright light stimulus is greater than approximately 2000 lux.

12. The method of claim 1, wherein said stimulus is applied to said subject for greater than approximately one hour.

13. The method of claim 12, wherein said stimulus is applied to said subject for approximately one to four hours.

14. The method of claim 1, wherein said measured melatonin content of said first and second samples is compared by plotting on a graph.

15. The method of claim 1, wherein said stimulus is applied to a retina of said subject.

16. A method of determining the functional integrity of the visual system of a visually impaired human subject by measuring the melatonin secretion of said subject, comprising the steps of:

predicting the minimum of the endogenous circadian temperature cycle of said visually impaired human subject;

collecting a first blood sample from said subject;

thereafter exposing said subject to a bright light stimulus of greater than approximately 4500 lux at approximately 1.5 hours before the predicted minimum of the endogenous circadian temperature cycle of said subject;

collecting a second blood sample from said subject during said exposure to said stimulus;

collecting a third blood sample from said subject after said exposure to said stimulus;

measuring the melatonin content in said first, second and third collected samples; and comparing the measured melatonin content in said first, second and third collected samples to determine whether said measured melatonin content in said second collected sample is less than said measured melatonin content in said first and/or third collected sample to evaluate the functional integrity of the visual system of said subject.

17. The method of claim 16, wherein said bright light stimulus is approximately 5000 to 10,000 lux.

18. The method of claim 16, wherein a plurality of first, second and third blood samples are collected.

19. The method of claim 18, wherein said plurality of blood samples are collected at approximately thirty minute intervals.

20. The method of claim 16, wherein said stimulus is applied to a retina of said subject.

* * * * *